United States Patent [19]

Khan et al.

[11] Patent Number: 5,136,031

[45] Date of Patent: Aug. 4, 1992

[54] CHLORINATION OF SUGARS

[75] Inventors: Riaz A. Khan, Sonning; George H. Sankey, Reading; Philip J. Simpson, Tadley; Nicholas M. Vernon, Barnard Castle, all of Great Britain

[73] Assignee: Tate & Lyle Public Limited Company, London, Great Britain

[21] Appl. No.: 474,314

[22] Filed: Jul. 9, 1990

[51] Int. Cl.$^5$ .......................... C07H 1/00; C07H 5/02; C07H 1/06; C07H 15/00

[52] U.S. Cl. .................... 536/122; 536/120; 536/119; 536/18.4; 536/124; 536/125; 536/4.1

[58] Field of Search ............... 536/122, 120, 124, 4.1, 536/18.4, 119, 125

[56] References Cited

U.S. PATENT DOCUMENTS

| | | | |
|---|---|---|---|
| 4,362,869 | 12/1982 | Jenner et al. | 536/125 |
| 4,380,476 | 4/1983 | Mufti et al. | 536/119 |
| 4,801,700 | 1/1989 | Tully et al. | 536/122 |
| 4,826,962 | 5/1989 | Rathbone et al. | 536/122 |
| 4,977,254 | 12/1990 | Homer et al. | 536/120 |
| 4,980,463 | 12/1990 | Walkup et al. | 536/120 |

OTHER PUBLICATIONS

Darzens, Comptes Rendues, 1911, 152, 1314, 1601; and 1912, 154, 1615, "Chimie Organique-Nouvelle methode d'etherification des alcools par les hydracides".
Gerrard, J. Chem. Soc. 1939, 99, "Studies on the Esters of Sulphurous Acid, etc. Part I"; 1940, 218 Studies on the Esters of Sulphurous, Chlorosulphinic, and Chlorosulphonic Acids. Part II; and 1944, 85, Experiments on the Interaction of Hydroxy-compounds and Phosphorus and Thionyl Halides in the Absence and in the Presence of Teriary Bases. Part I. Optically Active $\beta$-Octanol, Ethyl Madelate, and Phenylmethylcarbinol.

*Primary Examiner*—Ronald W. Griffin
*Assistant Examiner*—Louise Leary
*Attorney, Agent, or Firm*—Ostrolenk, Faber, Gerb & Soffen

[57] ABSTRACT

A process for the chlorination of sucrose or a derivative thereof, comprises reaction of the sucrose or derivative thereof with thionyl chloride and a nitrogen base at a ratio of about 1 molar equivalent (ME) of thionyl chloride and about 1 ME of base for every ME of free hydroxyl, in a non-reactive moderately polar solvent. The process is particularly suitable for the preparation of sucralose.

16 Claims, No Drawings

CHLORINATION OF SUGARS

This invention relates to the chlorination of sugars to produce chlorodeoxy derivatives, and in particular to the chlorination of sucrose derivatives in the preparation of sucralose (4,1'6'-trichloro-4,1',6'-trideoxy galacto sucrose).

There are a number of processes for the preparation of sucralose, all of which involve chlorination of the sucrose molecule in the 4-, 1'-, and 6'- positions. In order to achieve this, it is essential that the 6-position on the sucrose molecule is protected, since the 6-hydroxy group, being a primary hydroxy group, is highly reactive to chlorinating reagents. Some of these processes are described in U.S. Pat. 4,038,476 and GB 2,079,749, and GB 2,181, 734A.

In the chlorination of all 6-substituted sucrose derivatives, there is also the problem that it is not easy to obtain the correct degree of chlorination, i.e. to chlorinate not only at the primary 6'-hydroxy groups, but also at the secondary (and somewhat sterically hindered) 4-position, and the primary 1'-position, yet not at the other positions.

We have now found that a modification of a long-known chlorination technique can be used to give the required chlorinated products in good yields.

Chlorination of alcohols using thionyl chloride and pyridine has been known for very many years (Darzens, Comptes Rendues, 1911, 152, 1314, 1601; and 1912, 154, 1615). The mechanism of the process was explained by Gerrard (Gerrard, J. Chem. Soc. 1939, 998; 1940, 218; and 1944, 85). In a first stage, two alcohol molecules ROH react with thionyl chloride to form a sulphite $R_2SO_3$ and two molecules of hydrogen chloride which react with the pyridine to form pyridine hydrochloride. In a second stage, the sulphite is decomposed by reaction with further thionyl chloride to provide two molecules of a chlorosulphite $RSO_2Cl$. In a third stage, the chlorosulphites react with pyridine hydrochloride to provide two molecules of chloride RCl and two molecules of sulphur dioxide.

Thus, in the Darzens process, pyridine acts as a solvent for the reactants, as an acid acceptor for the hydrogen chloride released during the initial reaction of thionyl chloride with the alcohol to form the sulphite and, in the form of pyridine hydrochloride, as a catalyst for the release of chloride ions for the last stage of the reaction. For polyhydroxy compounds where large quantities of hydrogen chloride are released the action of pyridine as an acid acceptor prevents degradation of the polysulphite.

When this process is applied to polyhydroxy compounds such as sugars, it might be expected that intramolecular sulphites are produced, and in practice the result is always an exceedingly complex mixture of products. It is presumably for this reason that there appears to be no published example of the thionyl chloride-pyridine reagent system being used successfully to chlorinate sugars. The nearest approach is seen in the process of GB 2,181,734 A, which uses triphenyl phosphine oxide in conjunction with thionyl chloride and pyridine to chlorinate raffinoise but, as mentioned above, the results are far from satisfactory.

We have now found that sucrose protected at the 6-position, or sucrose itself, can be reacted with thionyl chloride and a base such as pyridine or an alkyl-substituted pyridine to provide a good yield of the required chlorinated product, provided certain conditions are met.

Firstly, the amounts of thionyl chloride and of pyridine should be approximately 1 molar equivalent (ME) for every free hydroxyl group in the sugar molecule. Thus, a sucrose 6-ester, having 7 free hydroxyl groups (of which 3 are to be chlorinated) should be reacted with about 7 ME of thionyl chloride and about 7 ME of pyridine. Similarly, raffinose, having 11 free hydroxyl groups (of which 4 are to be chlorinated), should be reacted with about 11 ME of thionyl chloride and about 11 ME of pyridine.

In practice, the amount can vary to a certain extent. In general, for a sucrose derivative having n free hydroxyl groups, it is desirable to use from 0.9 n to 1.2 n ME of thionyl chloride and from n to 1.4 n ME of pyridine, particularly n to 1.1 n of thionyl chloride and n to 1.3 n of pyridine.

Secondly, the reaction should be proceed in a non-reactive solvent in which the chlorosulphite is readily soluble, of moderate polarity. Chlorinated hydrocarbons such as partially chlorinated ethanes are preferred solvents, with 1,1,2-trichloroethane being most preferred because it offers shorter reaction times (e.g. two hours or less at a reflux temperature of 112°). 1,2-Dichloroethane is lower boiling (reflux 83°; reaction time 9-12 h) and, hence, less preferred.

The reaction is advantageously effected by gradual addition of a solution of the sucrose derivative in pyridine to a solution of thionyl chloride in the chemically inert solvent. The reaction should initially take place at a lower temperature, followed by a period at an elevated temperature, conveniently the reflux temperature of the mixture when the reaction is effected under atmospheric pressure (about 83° C. for 1,2-dichloroethane/pyridine and 112° C. for 1,1,2-trichloroethnae/pyridine).

Reference has been made to use of pyridine or alkyl-substituted pyridines in the reaction. We find that it is essential that an organic base is used. The base is necessary to neutralize hydrogen chloride which is evolved in the initial reaction of thionyl chloride with the hydroxyl group, which is believed to form an initial chlorosulphite and hydrogen chloride. Pyridine and alkyl-substituted pyridines, e.g., 3-picoline are particularly suitable because they are good solvents for the sugar derivatives. In a second phase of the reaction, the base hydrochloride acts as a source of chloride ions which displace the sulphite or chlorosulphite groups initially formed.

According to the present invention, therefore, we provide a process for chlorinating sucrose or a derivative thereof, particularly a 6- protected derivative such as a 6-ester or 6-ether, e.g. a glycosyl derivative such as raffinose, comprising reaction with thionyl chloride and a nitrogen base at a ratio of about one molar equivalent of thionyl chloride and about one molar equivalent of base for every molar equivalent of free hydroxyl in the sucrose or derivative thereof, in a non-reactive, moderately polar solvent. The method of the present invention provides an efficient and selective method of chlorinating sucrose 6-esters of use in the preparation of sucrose.

Thus, according to a further feature of the present invention there is provided a method for the preparation of sucralose comprising reaction of a 6-protected sucrose derivative with a chlorinating agent, characterized in that chlorination is effected by reaction with about one molar equivalent of thionyl chloride and about one molar equivalent of base for every molar equivalent of free hydroxyl in the sucrose derivative, in an inert, moderately polar, solvent.

EXAMPLE 1

Chlorination of sucrose with thionyl chloride and pyridine in 1,1,2-trichloroethane An heterogeneous mixture of sucrose (1 g) and pyridine (2.3 ml, 10 ME) was treated with thionyl chloride (1.7 ml, 8 ME) in 1,1,2-trichloroethane (4 ml) at 0° C. The reaction was brought to ambient temperature and then heated at 95° C. for 16 hr. The solution was neutralized with methanolic ammonia, concentrated to a syrup, and acetylated with acetic anhydride and pyridine at ambient temperature for 6 hr. The solution was concentrated, taken up in ether, washed with water, dried ($Na_2SO_4$), and concentrated to give a syrup (1.5 g). Glc analysis showed it to be a mixture of peracetates of 4,6,1',6'-tetrachloro-4,6,1',6'-tetradeoxygalactosucrose (26.4%), 4,6,6'-trichloro-4,6,6'-trideoxygalactosucrose (8.3%) and 6,6'-dichloro-6,6'-dideoxysucrose (17.0%).

EXAMPLE 2

Chlorination of sucrose 6-acetate

Sucrose 6-acetate (500 g; purity about 80%) was dissolved in pyridine (950 ml) and the solution was added to a stirred solution of thionyl chloride (730 ml) in 1,1,2-trichloroethane (TCE, 2000 ml) over 90 minutes, keeping the temperature below 20° C. The reaction mixture was then heated to reflux over 2 hours and held at reflux (112° C.) for 90 minutes. The mixture was then cooled to about 10° C. and water (1000 ml) was added over 30 minutes, keeping the temperature below 20° C. A mixture of ammonia (S.G. 0.880; 1700 ml) and water (500 ml) was then added over 60 minutes, keeping the temperature below 30° C. The mixture was then allowed to settle, the organic phase was separated off and the aqueous phase was extracted with a mixture of TCE and pyridine (4:1, 500 ml). The combined organic extracts were concentrated at 55° C. until about 1.5 liters of distillate had been collected and then cooled to about 20° C. Acetic anhydride (500 ml) was then added and the mixture was warmed to 60° C. More solvent (1000 ml) was then distilled off, xylene (2000 ml) was added and distillation was continued until a further 1000 ml of distillate had been removed. More xylene (1000 ml) was added, the mixture was cooled to about 25° C. and water (1000 ml) was added. The mixture was then seeded and cooled to 5° C. for 2 hours. The product was collected, washed with xylene (500 ml) and dried (fluid bed at 40° C.). Yield 570 g (damp); 524 g (dry); molar yield 65%. Assay 78.5% (by HPLC) with 13% xylene of crystallisation.

EXAMPLE 3

Preparation of 4',6-di-O-acetylsucrose

To a solution of sucrose-6-acetate (10 g) in pyridine (b 65 ml) was added isopropenyl acetate (30 ml) and lipase P Amano (20 g) and the reaction mixture was maintained at 60° C. for 6 days. TLC showed a 1:1 mixture of 6-O-acetylsucrose and 4', 6-di-O-acetylsucrose and a faster moving component, believed to be a sucrose triacetate. The enzyme was filtered off and the filtrate was concentrated to half its volume. Fresh enzyme (15 g) and pyridine (20 ml) were added and the reaction mixture was heated at 60° C. for 24 hours. TLC (ethyl acetate:acetone:water 8:6:1) indicated a yield of about 80% 4',6-di-O-acetylsucrose, with minor amounts of 6-O-acetylsucrose and two faster moving components. The enzyme was filtered off and the filtrate was concentrated to a syrup by co-distillation with toluene, then eluted from a column of silica gel with acetone followed by acetone containing 1% water to give 4',6-di-O-acetylsucrose (5.2 g, 47%).

EXAMPLE 3

Conversion of sucrose 6,4'-diacetate into Sucralose

A solution of sucrose 6,4'-diacetate in pyridine, was treated with thionyl chloride in 1,1,2-trichloroethane, initially at 0° C. for 0.5 h, and then at 95° C. for 4 h. The reaction mixture was diluted with methylene chloride, washed with cold aqueous sodium carbonate and then with water. The organic layer was dried ($Na_2SO_4$), concentrated by co-distillation with toluene, and then treated with 1M sodium methoxide in methanol (pH10.0) at room temperature for 4 h. T.l.c (ethyl acetate: acetone: water, 8:6:1) revealed sucralose as the major product, which was purified by silica gel chromatography and characterised by $^1$H-Nmr spectroscopy.

Comparative Example 1

Chlorination of sucrose 6-acetate with thionyl chloride and pyridine in 1,2-dichloroethane, using 9 ME thionyl chloride and 5 ME pyridine per ME sucrose 6-acetate Sucrose 6-acetate (5g; purity about 80%) was taken up in pyridine (5.6 ml; 5ME) and added dropwise over a period of 30 minutes to a stirred solution of thionyl chloride (9.1 ml; 9ME) in 1,2-dichloroethane (25ml), maintaining the temperature at −5° c. The mixture was allowed to warm to ambient temperature, then heated over one hour to reflux (83° C.). The solution was refluxed for 20 hours then concentrated to half volume. The concentrate was added to a cold mixture of ammonia (S.G. 0.880; 20 ml) and methanol (20 ml) and heated at 45° C. for 45 minutes. The solution was then concentrated to a thin syrup and partitioned between butanone (50 ml) and saturated aqueous ammonium chloride (50 ml). The aqueous layer was extracted with further butanone (50 ml) and the organic phases were combined, decolorised with Duolite DMF (H+/OH−) ion-exchange resin and concentrated to dryness. Analysis of the residue by HPLC showed a conversion of sucrose 6-acetate into sucralose and sucralose 6-acetate combined of about 5%.

COMPARATIVE EXAMPLE 2

Chlorination of sucrose-6-benzoate with 1.107 ME thionyl chloride and 0.1 ME 3-picoline per ME hydroxyl in 1,1,2-trichloroethane:

Sucrose-6-benzoate (2.50 g, 0.10 ME) was dissolved in 3-picoline (4.40 ml, 0.8 ME) and added dropwise to a solution of thionyl chloride (30.3 ml, 7.50 ME) in 1,1,2-trichloroethane (100 ml) over 5 minutes at 15° C. Solid sucrose-6-benzoate (22.5 g, 0.90 ME, i.e. a total of 1.0 ME of heptahydroxy material) was then added portionwise over 30 min to the solution at 15° C. No rise in temperature was observed. The sucrose-6-benzoate dissolved readily to give a clear, pale-yellow solution with copious gas emission. The mixture was heated to reflux (110° C.) over 50 min and refluxed for a total of 7.2 hr, monitoring the course of the reaction by tlc.

Considerable decomposition occurred and the reaction was stopped after 7.2 hr because of this.

The chlorination mixture was cooled to 20° C. and conc. aqueous ammonia (100 ml) was added dropwise over 1 hr, cooling the mixture to 30° C. After stirring for a further 4 hr at room temperature, water (100 ml) was added and the phases were separated. The organic phase was concentrated in vacuo to a black oil (11.1 g) which contained 22.1% sucralose-6-benzoate, along with residual picoline and various degradation products.

We claim:

1. A process for the chlorination of sucrose or a derivative thereof, in which the sucrose or derivative thereof is reacted with chlorinating agent consisting essentially of thionyl chloride and a nitrogen base at a ratio of about 1 molar equivalent (ME) of thionyl chloride and about 1 ME of base for every ME of free hydroxyl, in a non-reactive moderately polar solvent.

2. The process of claim 1 in which the ME ratio of thionyl chloride to free hydroxyl is from 0.9:1 to 1.2:1.

3. The process of claim 2 in which the said ME ratio is from 1:1 to 1.1:1.

4. The process of claim 2 in which the ME ratio of base to free hydroxyl is from 1:1 to 1.4:1.

5. The process of claim 1 in which the ME ratio of base to free hydroxyl is from 1:1 to 1.4:1.

6. The process of claim 5 in which the said ratio is from 1:1 to 1.3:1.

7. The process of claim 1 in which the nitrogen base is pyridine or an alkyl pyridine.

8. A process according to claim 1 in which the solvent is a chlorinated hydrocarbon.

9. The process of claim 8 in which the solvent is a partially chlorinated ethane.

10. The process of claim 9 in which the solvent is 1,1,2-trichloroethane.

11. The process of claim 1 in which the sucrose derivative is a 6- protected sucrose.

12. The process of claim 11, in which the 6- protected sucrose is selected from the group consisting of a 6-esther, 6-ether and a 6,4'-diester.

13. The process of claim 12 in which the 6-protected sucrose is selected from the group consisting of sucrose 6-acetate, sucrose 6-benzoate and raffinose.

14. In the process for the preparation of sucralose comprising reaction of a 6- protected sucrose derivative with a chlorinating agent in the presence of a nitrogen base and subsequently removing the 6- substituent, the improvement consisting in that the 6-substituted derivative is reacted with chlorinating agent consisting essentially of about one ME thionyl chloride and about one ME of base for every ME of free hydroxyl in the derivative.

15. The process of claim 14 in which the ME ratio of thionyl chloride to free hydroxyl is from 0.9:1 to 1.2:1 and the ME ratio of base to free hydroxyl is from 1:1 to 1.4:1.

16. The process of claim 15 in which the nitrogen base is pyridine or an alkyl pyridine.

* * * * *